US00PP22359P2

(12) United States Plant Patent
Pineau

(10) Patent No.: US PP22,359 P2
(45) Date of Patent: Dec. 20, 2011

(54) ***CHAMAECYPARIS* PLANT NAMED 'MINLEM'**

(50) Latin Name: *Chamaecyparis lawsoniana*
Varietal Denomination: Minlem

(75) Inventor: Patrick Pineau, Beaufort en Vallée (FR)

(73) Assignee: Pépinières Minier, Beaufort-en-Vallée (FR)

( * ) Notice: Subject to any disclaimer, the term of this patent is extended or adjusted under 35 U.S.C. 154(b) by 0 days.

(21) Appl. No.: 12/807,827

(22) Filed: Sep. 14, 2010

(51) Int. Cl.
*A01H 7/00* (2006.01)

(52) U.S. Cl. ..... Plt./213

(58) Field of Classification Search ..... Plt./213
See application file for complete search history.

(56) References Cited

OTHER PUBLICATIONS

Upov Plant Variety Database 2011/03. p. 1.*

* cited by examiner

*Primary Examiner* — Annette Para
(74) *Attorney, Agent, or Firm* — C. A. Whealy

(57) ABSTRACT

A new and distinct cultivar of *Chamaecyparis* plant named 'Minlem', characterized by its compact and rounded plant habit; freely branching habit; dense and bushy plant form; and young leaves that are greyed green in color becoming green with development and turning to yellow green in the autumn.

2 Drawing Sheets

Botanical designation: *Chamaecyparis lawsoniana.*
Cultivar denomination: 'MINLEM'.

BACKGROUND OF THE INVENTION

The present Invention relates to a new and distinct cultivar of *Chamaecyparis* plant, botanically known as *Chamaecyparis lawsoniana*, and hereinafter referred to by the name 'Minlem'.

The new *Chamaecyparis* plant is a naturally-occurring branch mutation of *Chamaecyparis lawsoniana* 'Ellwood's Gold', not patented. The new *Chamaecyparis* plant was discovered and selected by the Inventor during the summer of 2003 on a single plant of 'Ellwood's Gold' within a population of plants of 'Ellwood's Gold' in a controlled outdoor nursery environment in La Ménitré, Maine et Loire, France.

Asexual reproduction of the new *Chamaecyparis* plant by semi-hardwood cuttings in a controlled greenhouse environment in La Ménitré, Maine et Loire, France since December 2004, has shown that the unique features of this new *Chamaecyparis* plant are stable and reproduced true to type in successive generations.

SUMMARY OF THE INVENTION

Plants of the new *Chamaecyparis* have not been observed under all possible environmental conditions. The phenotype may vary somewhat with variations in environment and culture such as temperature and light intensity without, however, any variance in genotype.

The following traits have been repeatedly observed and are determined to be the unique characteristics of the new *Chamaecyparis* plant. These characteristics in combination distinguish 'Minlem' as a new and distinct cultivar of *Chamaecyparis* plant:

1. Compact and rounded plant habit.
2. Freely branching habit, dense and bushy plant form.

3. Young leaves that are greyed green in color becoming green with development and turning to yellow green in the autumn.

Plants of the new *Chamaecyparis* are most similar to plants of the parent, 'Ellwood's Gold'. In side-by-side comparison, slants of the new *Chamaecyparis* differ primarily from plants of 'Ellwood's Gold' in the following characteristics:

1. Plants of the new *Chamaecyparis* are more compact than and not as narrow and upright as 'Ellwood's Gold'.
2. Plants of the new *Chamaecyparis* have longer leaves than plants of 'Ellwood's Gold'.
3. In the autumn, leaves of plants of the new *Chamaecyparis* are brighter yellow green in color than leaves of plants of 'Ellwood's Gold'.

Plants of the new *Chamaecyparis* can also be compared to plants of *Chamaecyparis lawsoniana* 'Oregon Blue', not patented. Plants of the new *Chamaecyparis* differ from plants of 'Oregon Blue' in the following characteristics:

1. Plants of the new *Chamaecyparis* are more compact than and not as vigorous as plants of 'Oregon Blue'.
2. In the autumn, leaves of plants of the new *Chamaecyparis* are yellow green in color whereas leaves of plants of 'Oregon Blue' are blue green.

BRIEF DESCRIPTION OF THE PHOTOGRAPHS

The accompanying colored photographs illustrate the overall appearance of the new *Chamaecyparis* plant showing the colors as true as it is reasonably possible to obtain in colored reproductions of this type. Colors in the photographs may differ slightly from the color values cited in the detailed botanical description which accurately describe the colors of the new *Chamaecyparis* plant.

The photograph on the first sheet is a side perspective view of a typical plant of 'Minlem' grown in a container.

The photograph on the second sheet is a side perspective view of a typical plant of 'Minlem' (left) and a typical plant of 'Ellwood's Gold' (right) grown in containers.

DETAILED BOTANICAL DESCRIPTION

Plants used for the aforementioned photographs and following observations and measurements were grown in Grand Haven, Mich. during the summer in an outdoor nursery and under conditions which approximate commercial *Chamaecyparis* production. Plants were 1.5 years old when the photographs and description were taken. In the following description, color references are made to The Royal Horticultural Society Colour Chart, 1995 Edition, except where general terms of ordinary dictionary significance are used.

Botanical classification: *Chamaecyparis lawsoniana* 'Minlem'.

Parentage: Naturally-occurring branch mutation of *Chamaecyparis lawsoniana* 'Ellwood's Gold', not patented.

Propagation:

*Type.*—By semi-hardwood cuttings.

*Time to initiate roots.*—About four months at 10° C.

*Time to produce a rooted young plant.*—About six months at 13° C.

*Root description.*—Fine, fleshy; light brown in color.

*Rooting habit.*—Moderate branching; medium density.

Plant description:

*Form/growth habit.*—Compact evergreen shrub, rounded plant habit; moderately vigorous growth habit.

*Branching habit.*—Freely branching with numerous lateral branches developing per plant; dense and bushy plant form; plants maintain their lower branches and foliage at the soil level.

*Plant height.*—About 60 cm.

*Plant diameter.*—About 30 cm.

*Lateral branch description.*—Length: About 6 cm. Diameter: About 2.5 mm. Internode length: About 3 mm. Texture: Smooth, scaly. Strength: Strong, flexible. Color, developing: Close to 143A. Color, developed: Close to 137A.

*Leaf description.*—Arrangement: Whorled to alternate; sessile. Length: About 8 mm. Width: About 1 mm. Shape: Acicular. Apex: Acute. Base: Cuneate. Margin: Entire. Texture, upper and lower surface: Smooth, glabrous. Venation pattern: Parallel. Color: Developing leaves, upper and lower surfaces: Close to 189B to 189C. Fully expanded leaves, upper and lower surfaces: Close to 139B; venation, close to 139B; in the autumn, color becoming closer to 151A to 151B.

*Cone description.*—Cone development has not been observed.

Disease/pest resistance: Plants of the new *Chamaecyparis* have not been noted to be resistant to pathogens or pests common to *Chamaecyparis*.

Weather tolerance: Plants of the new *Chamaecyparis* have been observed to be tolerant to drought, rain, wind and temperatures ranging from about −20° C. to about 35° C.

It is claimed:

1. A new and distinct *Chamaecyparis* plant named 'Minlem' as illustrated and described.

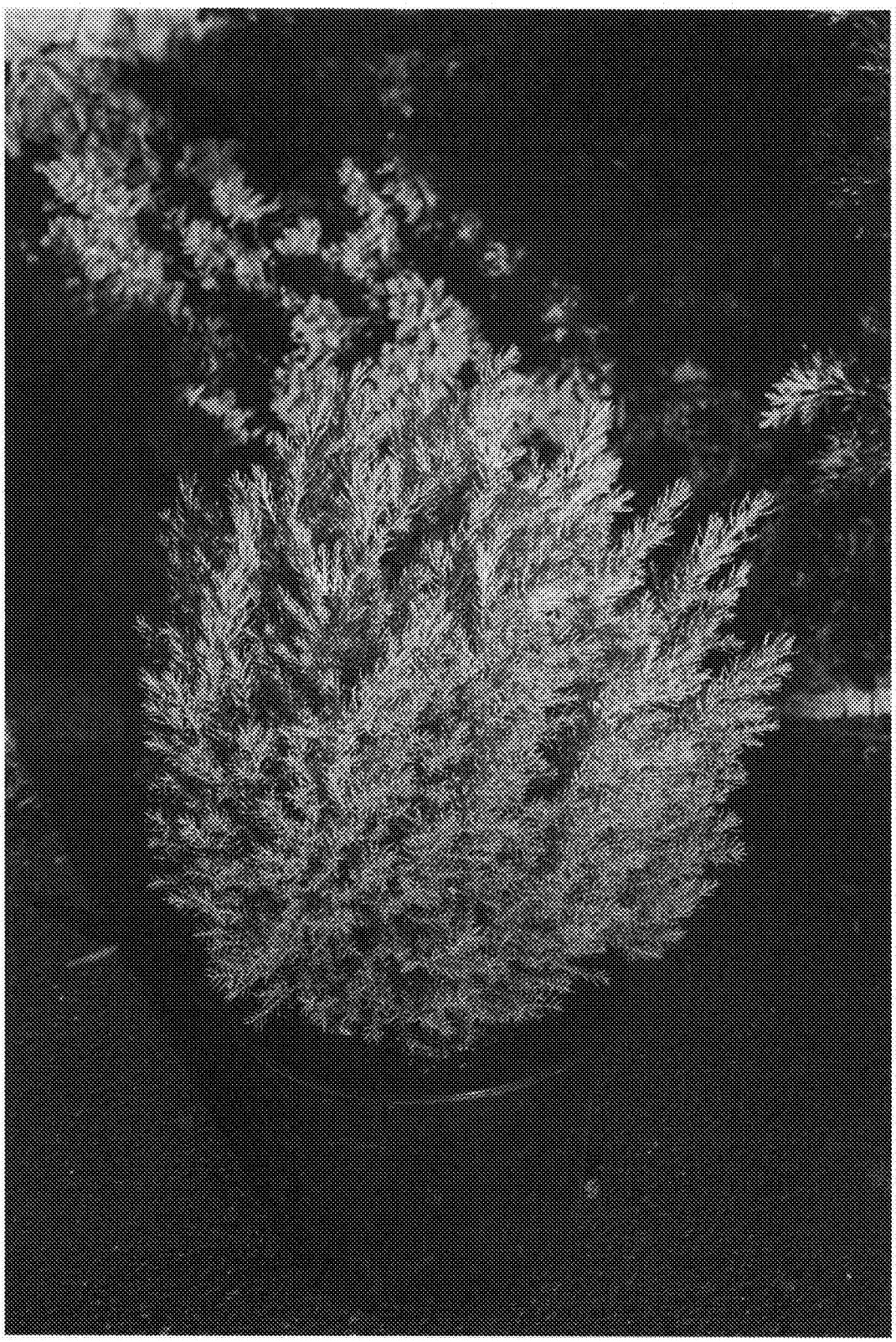

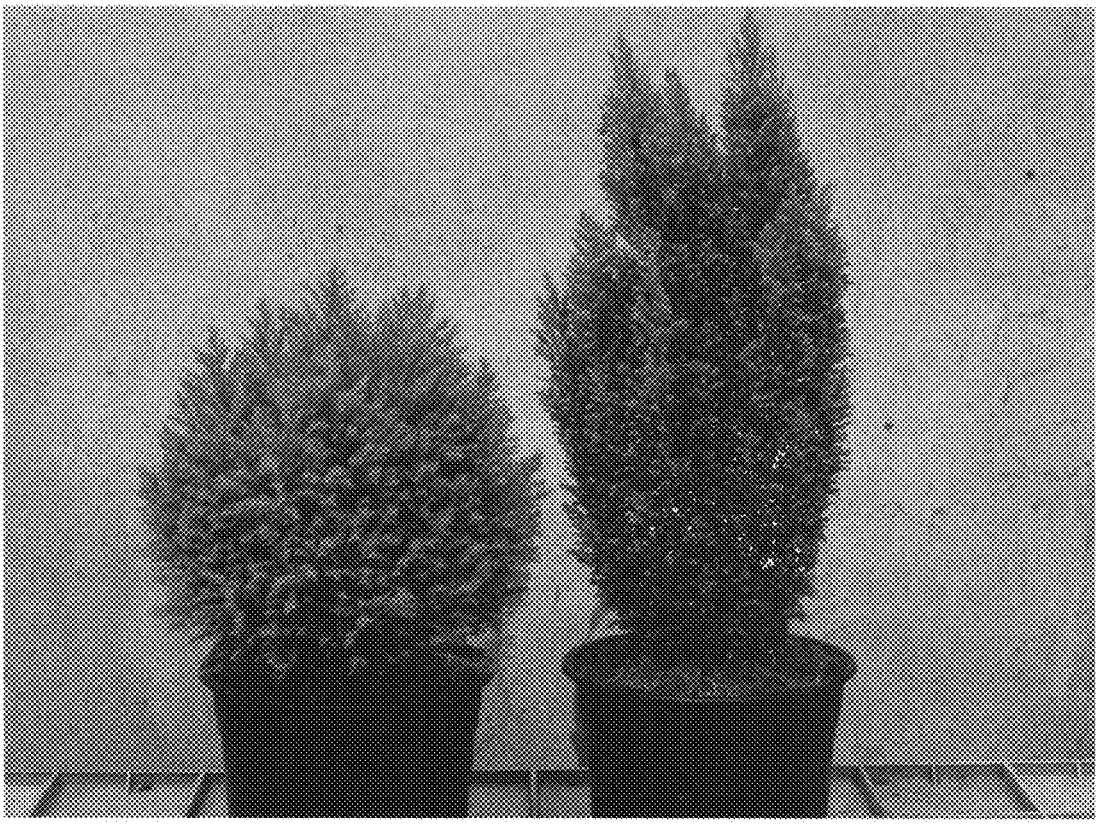

* * * * *